US005327195A

United States Patent [19]

Ehr

[11] Patent Number: 5,327,195
[45] Date of Patent: Jul. 5, 1994

[54] TRANSILLUMINATOR

[75] Inventor: Timothy G. J. Ehr, Menomonee Falls, Wis.

[73] Assignee: Fotodyne Incorporated, Hartland, Wis.

[21] Appl. No.: 40,530

[22] Filed: Mar. 31, 1993

[51] Int. Cl.$^5$ ............................................. G03B 27/04
[52] U.S. Cl. ................................................. 355/113
[58] Field of Search ................ 355/113, 114, 116, 118, 355/120

[56] References Cited

U.S. PATENT DOCUMENTS

| | | | |
|---|---|---|---|
| 3,352,222 | 11/1967 | Salger | 355/113 X |
| 4,071,883 | 1/1978 | Dennis | 362/97 |
| 4,657,655 | 4/1987 | Smoot et al. | 204/299 R |
| 5,117,257 | 5/1992 | Tjonneland | 355/91 |

OTHER PUBLICATIONS

Fotodyne 1991 Catalog; pp. 8-9.

*Primary Examiner*—Richard A. Wintercorn
*Attorney, Agent, or Firm*—Michael, Best & Friedrich

[57] ABSTRACT

A transilluminator including a housing with a top wall having a UV-transmissible window and an upwardly extending projection. A UV light source is supported within the housing for transmitting UV light through the window and a UV-blocking cover with a hinge assembly is provided for movement of the cover between a blocking position and a non-blocking position. The hinge assembly has an undercut, and the protector plate includes a rearward portion which extends into the undercut when the plate is positioned over the window. The plate also includes a forward portion having an aperture through which the projection extends when the plate is positioned over the window. The plate is secured to the top wall by sliding the rearward portion of the plate into the undercut and then lowering the forward portion of the plate so that the projection extends into the aperture. The plate is removed by raising the forward portion of the plate so that the projection is removed from the aperture and then sliding the rearward portion of the plate out of the undercut.

17 Claims, 1 Drawing Sheet

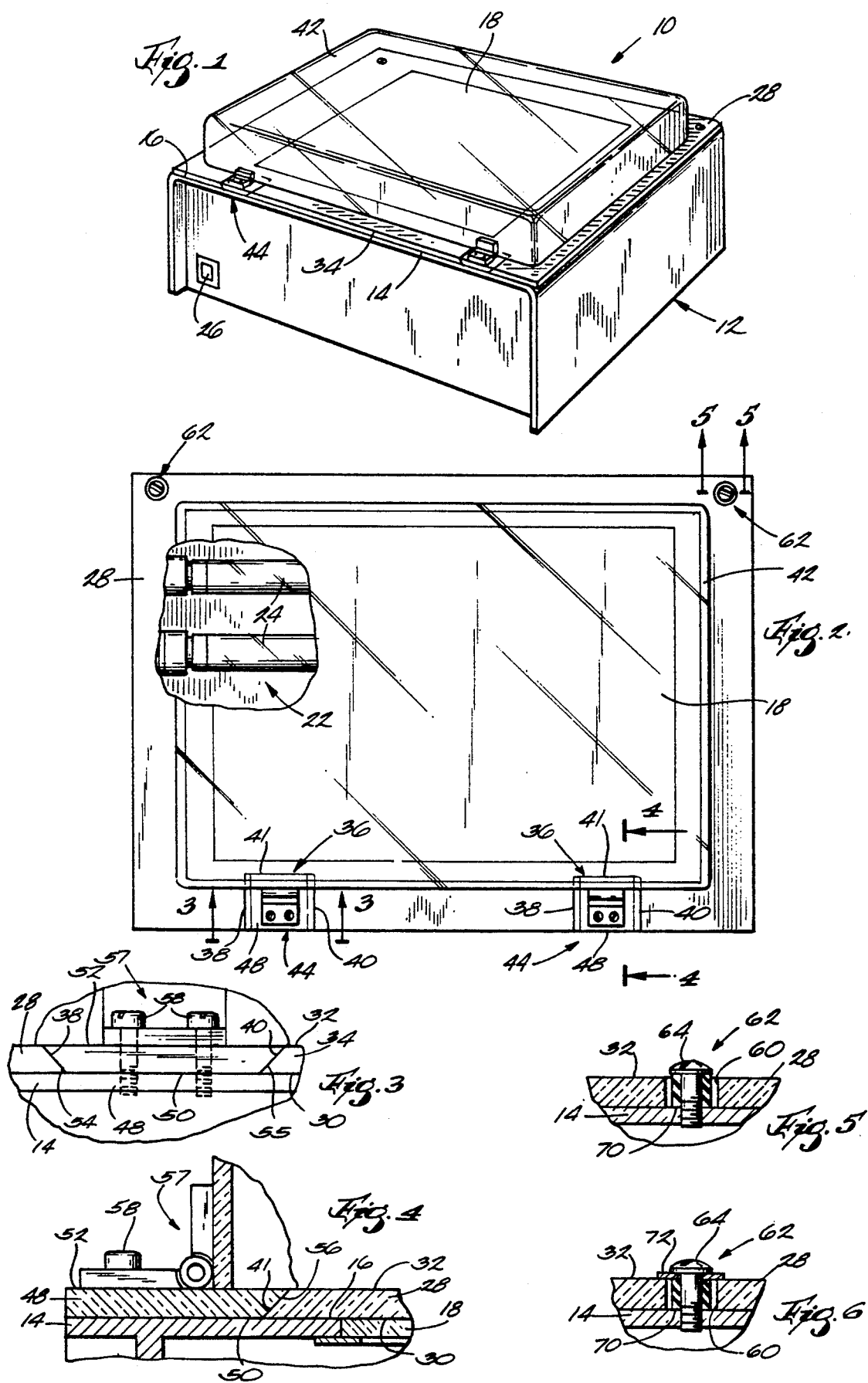

//5,327,195

TRANSILLUMINATOR

BACKGROUND OF THE INVENTION

This invention relates to transilluminators for use with visualizing DNA in agarose gels.

A common method for separating, identifying or purifying DNA from a mixed sample is by electrophoresis of the sample through an agarose gel. The electrophoretic migration rate of DNA through agarose gel is dependent upon the molecular weight of the DNA, as well as such considerations as the agarose concentration and the strength of the electric field. The electrophoresis technique is simple and rapid, and results in the formation of distinct bands of DNA within the gel.

After electrophoresis for a sufficient period, electrophoresis gels are typically stained to visualize the bands of DNA, often with low concentrations of the fluorescent dye ethidium bromide. Ethidium bromide, which becomes bound-up, or intercalated, between bases of the DNA, has an increased fluorescent yield, as compared to free ethidium bromide in solution. UV radiation is absorbed by bound ethidium bromide dye and re-emitted in the red-orange region of the visible spectrum. Thus, the location and relative amount of DNA is detectable by direct examination of an ethidium bromide-stained electrophoresis gel under illumination by ultraviolet light.

One apparatus used to illuminate electrophoresis gels produces ultraviolet light in a closed box. A light source within the box transmits UV light through a horizontal window provided in the top of the box. A gel is positioned over the window for illumination by the UV light, which passes through the gel from the window below. Such an apparatus is referred to as a transilluminator.

The window of the transilluminator typically comprises a purple filter glass centered directly over the UV light source. This filter glass blocks all light except that within a narrow range centered around the specific UV region which causes the fluorescence of ethidium bromide bound to DNA. The filter glass is a relatively expensive component of the transilluminator. Physical damage to the glass can occur when researchers cut out DNA-containing bands of gel while the gel is illuminated on the glass, or can be the result of accidental contact such as from dropping small objects onto the top of the transilluminator. Such damage to the glass surface can affect background UV transmission through the glass. Problems with the glass surface can also arise from permanent staining or contamination by laboratory fluids, gel fragments or residual DNA from gels, which can result in clouding of the glass or in high levels of background fluorescence.

Since the glass surface can easily become damaged from physical contact or contamination, all of which will impair the accurate measurement of DNA within the gels, an inexpensive and easily cleaned protector plate is often placed over the top of the transilluminator. The plate shields the filter glass from accidental physical contact and keeps gels from directly contacting the UV filter during transillumination. There is no significant loss of sensitivity of DNA detection when the protector plate is in place. The protector plate is typically held in place on the surface of the transilluminator by screws, or, if a less permanent mounting is acceptable, by magnetic strips. As the protector plate becomes clouded or damaged, it is replaced, at a far smaller cost than if the filter glass is replaced.

The visualization of ethidium bromide-stained DNA samples on agarose gels with UV light creates a risk to the researcher of eye or skin damage from exposure to the UV radiation. In U.S. Pat. No. 4,657,655, a transilluminator is shown having a cover made of a UV radiation blocking material. This cover greatly reduces the risk of eye and skin damage from UV radiation, thus eliminating the necessity for cumbersome protective equipment for the researcher, such as face shields or eyeglasses.

When such a blocking cover is utilized, the plate protecting the filter glass is permanently mounted on the transilluminator surface by screws set into the housing. These screws allow for replacement of the protector plate as it becomes damaged over time, or even if the researcher simply wishes, for whatever reason, to utilize the transilluminator without the protector plate. The blocking cover is also connected to the top wall of the housing by a hinge which is secured to the top wall by screws which pass through the protector plate covering the top surface of the transilluminator. Thus, to remove the protector plate one must remove both the hinge and blocking cover.

SUMMARY OF THE INVENTION

Even when the blocking cover is not utilized, for many applications the protector plate will need to be more firmly secured to the surface than through magnetic strips. For various reasons, transilluminators are often moved about by the researcher, such as to and from a photographic darkroom. For these reasons it is desirable to secure the protective cover to the transilluminator in such a fashion that the protective cover can not be removed inadvertently, but only by the deliberate actions of the researcher. However, it is also desirable that the researcher be able to remove the protector plate, such as for performing a cross-linking procedure or for cleaning, without involving tools to remove and replace the screws securing the protector plate and blocking cover to the housing.

An object of the present invention is, thus, to provide a selectively and easily removable protector plate for a UV transilluminator. In accordance with the invention, a transilluminator is provided comprising a housing including a top wall having a UV-transmissible window. A UV light source is supported within the housing for transmitting UV light through the window, and a UV-blocking cover is provided with a hinge assembly pivotally connecting the cover to the top wall for movement between a blocking position and a nonblocking position. The hinge assembly is also provided with an undercut.

The transilluminator also comprises a protector plate including a rearward portion with a notch which receives the hinge assembly and which is defined by a side wall that extends into the undercut of the hinge assembly when the plate is positioned over the window. Such interengagement of the plate and the hinge assembly prevents upward movement of the plate at the hinge assembly.

The top wall of the housing preferably includes an upwardly extending projection, such as a screw, with the plate having therethrough an aperture through which the screw extends when the plate is positioned over the window and engaged with the undercut of the hinge assembly. Location of the screw in the aperture prevents lateral movement of the plate and thereby prevents disengagement of the plate and the hinge assembly.

The plate is easily secured to the top wall by sliding the rearward portion of the plate into the undercut and then lowering the forward portion of the plate so that the screw extends through the aperture. The plate is easily removed from the top wall by reversing this action, by raising the forward portion of the plate so that the screw is removed from the aperture, and then sliding the rearward portion of the plate out of the undercut.

The transilluminator preferably includes a washer having an outer diameter greater than the inner diameter of the aperture. The washer can be utilized in surrounding the screw between the screw head and the plate upper surface, to prevent upward movement of the plate relative to the top wall of the housing, when that arrangement is desired. The washer is removable from the screw so that upward movement of the plate relative to the top wall of the housing is possible and easily permits removal of the plate by a forward sliding action.

A principal feature of the invention is the provision of a transilluminator with means for securing the protector plate to the housing such that the plate is manually removable from the housing without tools.

Another principal feature of the invention is the provision of a transilluminator with selectively engageable means for preventing removal of the plate from the housing without tools.

Another principal feature of the invention is the provision of a transilluminator with a hinge assembly connecting a UV-blocking cover to the housing, and means for securing the protector plate to the housing such that the plate is removable without removing the hinge assembly.

Other features and advantages of the invention will become apparent to those skilled in the art upon review of the following detailed description and claims.

BRIEF DESCRIPTION OF THE DRAWINGS

FIG. 1 is a perspective view of a transilluminator embodying the invention.

FIG. 2 is a top plan view of the transilluminator showing the protector plate and blocking cover.

FIG. 3 is a view taken along line 3—3 in FIG. 2.

FIG. 4 is a view taken along line 4—4 in FIG. 2.

FIG. 5 is a view taken along line 5—5 in FIG. 2.

FIG. 6 is a view similar to FIG. 5 showing a washer beneath the screw head.

Before one embodiment of the invention is explained in detail, it is to be understood that the invention is not limited in its application to the details of construction and the arrangement of components set forth in the following description or illustrated in the drawings. The invention is capable of other embodiments and of being practiced or carried out in various ways. Also, it is to be understood that the phraseology and terminology used herein is for the purpose of description and should not be regarded as limiting.

DESCRIPTION OF THE PREFERRED EMBODIMENT

The drawings illustrate a transilluminator 10 embodying the invention. As seen in FIG. 1, the transilluminator 10 generally comprises a housing 12 having a top wall 14 forming an upper surface 16. The top wall 14 has therein a UV-transmissible window 18 preferably made of a purple filter glass. A UV light source 22 (FIG. 2) is supported within the housing 12 for transmitting UV light through the window 18. The light source 22 preferably comprises one or more fluorescent lamps 24. Again referring to FIG. 1, a manual switch 26 is provided on the front of the housing 12 to energize the lamps 24. A cooling fan (not shown) is preferably also incorporated within the housing to prevent thermal damage to the DNA fragments, the agarose gel or other transilluminator components during transillumination.

A protector plate 28 overlies the window 18 and is attached to the housing surface 16. The plate 28 preferably comprises a plexiglass transparent to both visible spectrum and UV radiation. The UV transparent plate 28 generally protects and preserves the expensive UV filter glass of the window 18, and enables the researcher to cut out gel slices containing bands of DNA without damaging the glass itself. If the protector plate 28 becomes scratched, otherwise damaged, overly contaminated or clouded from solarization it can be simply removed and discarded. The cost for a replacement plate is a fraction of the cost for replacement of the UV glass of the window 18.

As seen in FIGS. 2-4, the protector plate 28 has a generally horizontal lower surface 30, a generally horizontal upper surface 32 and an endless side wall 34 connecting the lower and upper surfaces 30 and 32, respectively. The side wall 34 is recessed to define two notches 36 each having opposed side surfaces 38 and 40 and a front surface 41, all of which are part of the side wall 34. As shown in FIGS. 3 & 4, the notch surfaces 38, 40 and 41 taper outwardly from the lower protector plate surface 30 to the upper protector plate surface 32.

In the preferred embodiment, the transilluminator comprises a UV-blocking cover 42 (FIG. 1) designed to shield the user from damaging UV radiation from the light source 22. The blocking cover 42 is made of an ultraviolet filtering material such as acrylic plastic. The cover 42 may be molded, such as from a ¼", W-blocking plexiglass. As best illustrated in FIGS. 1-4, two hinge assemblies 44 pivotally connect the cover 42 to the housing 12 for movement of the cover 42 between blocking and non-blocking positions. While two hinge assemblies 44 are shown, it should be understood that only one or more than two can be employed. With the cover 42 in the blocking position, i.e., flush against the housing 12, it is possible for several researchers or students to observe a gel with no risk of harmful exposure to UV radiation. The cover 42 can preferably be set at any angle to allow easy access to the gel, as is necessary. The cover 42 can be quickly and easily adjusted to any position from flush with the protector plate surface 32 up to a 90 degree or greater angle with the surface 32, as desired.

Each hinge assembly 44 includes a hinge block 48 (FIGS. 3 and 4) mounted on the housing upper surface 16. The hinge block 48 has a generally horizontal lower surface 50 engaging the housing upper surface 16. The hinge block 48 has a generally horizontal upper surface 52, and opposed side surfaces 54 and 55 and a front surface 56 connecting the upper and lower hinge block surfaces 50 and 52. The opposed side surfaces 54 and 56 and the front surface 56 taper outwardly from the lower hinge block surface 50 to the upper hinge block surface 52. Each of the surfaces 54, 55 and 56 defines an undercut in the hinge block. Each hinge assembly 44 also includes a hinge 57 pivotally connecting the cover 42 to the upper hinge block surface 52. Each hinge assembly 44 is secured to the housing 14 by suitable means such as screws 58.

The transilluminator 10 includes means for securing the plate 28 to the upper surface 16 of the housing 12 such that the plate 28 is manually removable from the housing surface 16 without tools. In the illustrated embodiment the securing means includes inter-engaging means on the hinge assemblies 44 and on the plate 28 (FIG. 3). While various inter-engaging means may be employed, in FIG. 3 such means includes location of each hinge block 48 in an associated protector plate notch 36, with the tapered hinge block surfaces 54, 55 and 56 respectively mating in a complementary fashion with the side wall surfaces 38, 40 and 41 of the notch 36. Thus, the plate 28 includes rearward portions extending into the undercuts defined by the surfaces 54, 55 and 56. The close mating of the tapered surfaces 54, 55, 56, 38, 40 and 41 prevents upward movement of the protector plate 28 relative to the housing 12 adjacent the hinge assemblies 44. The side surfaces 54 and 55 of the hinge block prevent lateral movement of the plate 28, and the front surface 56 of the hinge block prevents rearward movement of the plate 28. In this fashion, movement of the plate 28 relative to the housing 12 is allowed in only the forward direction (up in FIG. 2) with respect to the housing top wall 14.

Selectively disengageable means are also provided for preventing forward movement of the protector plate 28 relative to the housing 12. While various means may be employed, in the illustrated embodiment (FIG. 5) the protector plate 28 has therethrough apertures 60 extending from the protector plate upper surface 32 to the protector plate lower surface 30, each aperture 60 having an inner diameter and being spaced from both notches 36 in the protector plate 28. The apertures are preferably located in the forward corners of the plate 28. The selectively disengageable means also includes projections 62 which extend upwardly from the upper surface 16 of the housing 12, each projection 62 having an outer diameter less than the inner diameter of each aperture 60. The projections are preferably screws having respective heads 64. When the protector plate 28 is properly positioned on the housing upper surface 16, each screw 62 extends through a respective aperture 60. A protective sleeve 70 is preferably placed around each screw 62 to protect the plate 28 from chipping against the screw 62.

Forward movement of the protector plate 28 relative to the housing 12 is allowed only after upward movement of the forward portion of the plate 28 relative to the housing 12. The upward movement of the forward portion of the protector plate 28 removes the screws 62 from the apertures 60. The protector plate 28 should be produced of a somewhat flexible material, for as the forward portion of the protector plate 28 is moved upward the rearward portion of the protector plate 28 is held against such movement by the hinge blocks 48.

The transilluminator 10 also comprises selectively disengageable means for preventing removal of the protector plate 28 from the housing 12 without tools. Such means preferably includes selectively disengageable means for preventing upward movement of the forward portion of the plate 28 relative to the housing 12. More particularly, as shown in FIG. 6, a washer 72 having an outer diameter greater than the inner diameter of the aperture 60, surrounds each screw 62 between the head 64 and the protector plate upper surface 32 so as to prevent upward movement of the protector plate 28 relative to the housing top wall 14.

When the washers 72 are removed, upward movement of the forward portion of the protector plate 28 is allowed, thereby permitting forward movement of the protector plate 28. Such forward movement disengages the plate 28 and the hinge blocks 48, so that the plate 28 no longer extends into the undercuts in the hinge blocks 48. Removal of the protector plate 28 from the housing 12 is thereby permitted when the washers 72 are removed.

What is claimed is:

1. A transilluminator comprising
a housing having therein a UV-transmissible window,
a UV light source supported within said housing for transmitting UV light through said window,
a protector plate overlying said window,
means for securing said plate to said housing such that said plate is manually removable from said housing without tools, and
selectively engageable means for preventing removal of said plate from said housing without tools.

2. A transilluminator as set forth in claim 1 wherein said securing means includes restraining means for allowing movement of said plate relative to said housing in only one direction.

3. A transilluminator as set forth in claim 2 wherein said restraining means allows movement of said plate relative to said housing in said one direction only after movement of said plate relative to said housing in a second direction transverse to said one direction.

4. A transilluminator as set forth in claim 2 wherein said securing means also includes selectively disengageable means for preventing movement of said plate relative to said housing in said one direction.

5. A transilluminator as set forth in claim 1 wherein said protector plate has therethrough an aperture having an inner diameter, wherein said securing means includes a projection which extends from said housing and through said aperture, which has a head, and which has an outer diameter less than said inner diameter of said aperture, and wherein said selectively disengageable means includes a washer having an outer diameter greater than said inner diameter of said aperture, said washer surrounding said projection between said head and said protector plate so as to prevent movement of said protector plate relative to said housing, and said washer being removable from said projection so as to allow movement of said protector plate relative to said housing.

6. A transilluminator comprising
a housing having therein a UV-transmissible window,
a UV light source supported within said housing for transmitting UV light through said window,
a UV-blocking cover,
a hinge assembly pivotally connecting said cover to said housing for movement between a blocking position and a non-blocking position,
a protector plate overlying said window, and
means for securing said plate to said housing such that said plate is removable from said housing without removing said hinge assembly from said housing.

7. A transilluminator as set forth in claim 6 wherein said housing has an upper surface having therein said window, wherein said hinge assembly is secured to said upper surface, and wherein said securing means secures said plate to said upper surface.

8. A transilluminator as set forth in claim 7 wherein said securing means includes inter-engaging means on said hinge assembly and on said plate.

9. A transilluminator as set forth in claim 8 wherein said inter-engaging means includes restraining means for allowing movement of said plate relative to said housing in only one direction.

10. A transilluminator as set forth in claim 9 wherein said restraining means allows movement of said plate relative to said housing in said one direction only after movement of said plate relative to said housing in a second direction transverse to said one direction.

11. A transilluminator as set forth in claim 9 wherein said securing means also includes selectively disengageable means for preventing movement of said plate relative to said housing in said one direction.

12. A transilluminator as set forth in claim 8 wherein said hinge assembly includes a hinge block mounted on said upper surface, said hinge block having a generally horizontal lower surface engaging said upper surface, a generally horizontal upper surface, and a pair of opposed side surfaces connecting said upper and lower hinge block surfaces and tapering outwardly from said lower hinge block surface to said upper hinge block surface, wherein said hinge pivotally connects said cover to said upper hinge block surface, wherein said protector plate has a generally horizontal lower surface, a generally horizontal upper surface and an endless side wall connecting said upper and lower protector plate surfaces, said side wall including opposed surfaces defining a notch receiving said hinge block, said opposed side wall surfaces tapering outwardly from said lower protector plate surface to said upper protector plate, said side wall surfaces and said hinge block side surfaces mating in complementary fashion so as to prevent relative upward movement of said protector plate relative to said housing.

13. A transilluminator as set forth in claim 12 wherein said protector plate has therethrough an aperture extending from said protector plate upper surface to said protector plate lower surface, said aperture having an inner diameter and being spaced from said notch, and wherein said securing means also includes a projection which extends upwardly from said upper surface of said housing and through said aperture and which has an outer diameter less than said inner diameter of said aperture.

14. A transilluminator as set forth in claim 13 wherein said projection is a screw having a head, and wherein said transilluminator also comprises a washer having an outer diameter greater than said inner diameter of said aperture, said washer surrounding said screw between said head and said protector plate upper surface so as to prevent upward movement of said protector plate relative to said top wall of said housing, and said washer being removable from said screw so as to allow upward movement of said protector plate relative to said top wall of said housing, thereby permitting lateral movement of said protector plate relative to said top wall to remove said hinge block from said notch and allow removal of said protector plate from said housing.

15. A transilluminator comprising
a housing including a top wall having therein a UV-transmissible window and having thereon an upwardly extending projection,
a UV light source supported within said housing for transmitting UV light through said window,
a UV-blocking cover,
a hinge assembly pivotally connecting said cover to said top wall for movement between a blocking position and a non-blocking position, said hinge assembly having therein an undercut, and
a protector plate including a rearward portion which extends into said undercut when said plate is positioned over said window, and said plate also including a forward portion having therethrough an aperture through which said projection extends when said plate is positioned over said window,
such that said plate is secured to said top wall by sliding said rearward portion of said plate into said undercut and then lowering said forward portion of said plate so that said projection extends into said aperture, and such that said plate is removed from said top wall by raising said forward portion of said plate so that said projection is removed from said aperture and then sliding said rearward portion of said plate out of said undercut.

16. A transilluminator as set forth in claim 15 wherein said plate has an upper surface, wherein said aperture has an inner diameter, wherein said projection is a screw having a head, and wherein said transilluminator further comprises a washer having an outer diameter greater than said inner diameter of said aperture, said washer surrounding said screw between said head and said plate upper surface so as to prevent upward movement of said plate relative to said top wall of said housing, and said washer being removable from said screw so as to allow upward movement of said plate relative to said top wall of said housing.

17. A transilluminator comprising
a housing including a top wall having a generally horizontal upper surface and having therein a UV-transmissible window,
a UV light source supported within said housing and beneath said window,
a hinge block mounted on said upper surface, said hinge block having a generally horizontal lower surface engaging said upper surface of said top wall, a generally horizontal upper surface, and a pair of opposed side surfaces connecting said upper and lower hinge block surfaces and tapering outwardly from said lower hinge block surface to said upper hinge block surface,
a UV-blocking cover,
a hinge pivotally connecting said cover to said upper hinge block surface for movement between a blocking position and a non-blocking position,
a protector plate overlying said top wall upper surface and having a generally horizontal lower surface, a generally horizontal upper surface and an endless side wall connecting said upper and lower protector plate surfaces, said side wall including opposed surfaces defining a notch receiving said hinge block, said opposed side wall surfaces tapering outwardly from said lower protector plate surface to said upper protector plate, said side wall surfaces and said hinge block side surfaces mating in complementary fashion so as to prevent relative upward movement of said protector plate relative to said top wall of said housing, and said protector plate having therethrough an aperture extending from said protector plate upper surface to said protector plate lower surface, said aperture having an inner diameter and being spaced from said notch, a screw which extends through said aperture and which is threaded into said top wall, said screw having a head with an outer diameter less than said inner diameter of said aperture, and a washer having an outer diameter greater than said inner diameter of said aperture, said washer surrounding said screw between said head and said protector plate upper surface so as to prevent upward movement of said protector plate relative to said top wall of said housing, and said washer being removable from said screw so as to allow upward movement of said protector plate relative to said top wall of said housing, thereby permitting lateral movement of said protector plate relative to said top wall to remove said hinge block from said notch and allow removal of said protector plate from said housing.

* * * * *